United States Patent [19]

Thomason et al.

[11] Patent Number: 5,496,335
[45] Date of Patent: Mar. 5, 1996

[54] INSERTABLE SUTURE PASSING GRASPING PROBE AND METHODOLOGY FOR USING SAME

[75] Inventors: Rodger Thomason, Los Angeles; James E. Carter, Mission Viejo; Mark J. Legome, Mission Viejo; Neil H. Naves, Mission Viejo, all of Calif.

[73] Assignee: Inlet Medical, Inc., Eden Prairie, Minn.

[21] Appl. No.: 112,585

[22] Filed: Aug. 25, 1993

[51] Int. Cl.⁶ .......................... A61B 17/04; A61B 17/28
[52] U.S. Cl. .......................... 606/148; 606/205
[58] Field of Search .................. 606/205, 206, 606/207, 144, 148, 151

[56] References Cited

U.S. PATENT DOCUMENTS

| | | |
|---|---|---|
| 3,577,991 | 5/1971 | Wilkinson . |
| 4,938,214 | 7/1990 | Specht et al. . |
| 4,950,273 | 8/1990 | Briggs . |
| 4,955,896 | 9/1990 | Freeman ......................... 606/207 |
| 5,147,373 | 9/1992 | Ferzli . |
| 5,171,256 | 12/1992 | Smith et al. . |
| 5,171,257 | 12/1992 | Ferzli . |
| 5,192,298 | 3/1993 | Smith et al. . |
| 5,196,023 | 3/1993 | Martin . |
| 5,201,743 | 4/1993 | Haber et al. . |
| 5,201,752 | 4/1993 | Brown et al. . |
| 5,201,759 | 4/1993 | Ferzli . |
| 5,211,655 | 5/1993 | Hasson ........................... 606/170 |
| 5,308,358 | 5/1994 | Bond et al. ..................... 606/207 |
| 5,342,391 | 8/1994 | Foshee et al. .................. 606/205 |

*Primary Examiner*—Stephen C. Pellegrino
*Assistant Examiner*—Nancy Mulcare
*Attorney, Agent, or Firm*—Cislo & Thomas

[57] ABSTRACT

A surgical instrument and method capable of being used for closure of peritoneum fascia, occlusion of bleeding vessels such as inferior epigastric, and for all uses related to passing of suture through tissue with the tip of the surgical instrument in a standard suture/needle driving position with a sharp tip that opens and closes with the surgeon grasping suture material with the sharp tip and inserting the tip/suture through tissue until the tip is seen through the peritoneum by direct vision wherein the suture is released by opening and withdrawing the tip and recovered by puncturing the tissue opposite the first point of insertion wherein the tip grasps the suture and pulls the suture outside the wound providing for rapid closure of the surgical incision.

8 Claims, 5 Drawing Sheets

INSERTABLE SUTURE PASSING GRASPING PROBE AND METHODOLOGY FOR USING SAME

The present invention relates to improvements in the procedure for suturing tissue during endoscopic/laparoscopic surgery. More particularly, the invention relates to a method of suturing which utilizes a modified laparoscopic grasper.

An endoscopic/laparoscopy procedure involves making small surgical incisions in a patient's body for the insertion of trocar tubes thereby creating access ports into the patient's body. Thereafter, various types of endoscopic/laparoscopic instruments are passed through these access ports and the appropriate surgical procedures are carried out.

After the surgical procedure is performed the trocar tubes are removed and the incisions sutured closed by using both a needle and grasper for penetrating the tissue and handling the suture. This procedure for closure is frequently a time-consuming procedure requiring the identification of the fascia and closure of each fascial site with suture from an external point.

The necessity for closing these port sites in laparoscopic surgery is critical since suturing the incisions improperly can lead to bowel herniation through the port sites as well as the possibility of omental trapping if the fascial sites are not properly closed. Incisional hernias have occurred in both laparoscopic-assisted vaginal hysterectomies and laparoscopic cholecystectomies as well as other advanced laparoscopic procedures.

Thus, there is a need for an endoscopic/laparoscopic instrument and method which will significantly reduce the operating time and is better able to give the surgeon direct visualization of the fascial and peritoneal closing. Additionally, there is a need for a surgical instrument which allows the surgeon to control bleeding sites by rapidly putting sutures around blood vessels of the abdominal wall.

The subject invention herein solves all of these problems in a new and unique manner which has not been part of the art previously. General types of surgical forceps and laparoscopic graspers are known in the art and some related patents directed to surgical instruments are described below:

U.S. Pat. No. 5,192,298 issued to W. Smith et al. on Dec. 15, 1992

This patent is directed to a disposable laparoscopic surgical instrument. The laparoscopic surgical instrument comprises a tube surrounded by a peripheral insulating shrink wrap layer, a clevis means, and effectors pivotally engaged to the clevis at a pivot pin, and activating means. The effectors are provided with blades or graspers which taper to a point and are rotatably mounted on the pivot pin.

U.S. Pat. No. 5,201,743 issued to T. Haber et al. on Apr. 13, 1993

This patent is directed to an axially extendable endoscopic surgical instrument. The endoscopic surgical instrument includes an elongate body, a tip carrier tube, a tip assembly removably mounted to the distal end of the carrier tube and having a pair of movable jaws, a driver assembly which causes jaws to move between open and closed positions, and a jaw rotating assembly which causes the tip assembly and jaws therewith to rotate about an axis. The jaws taper substantially at their distal ends and the interior surface of the jaws are serrated.

U.S. Pat. No. 4,950,273 issued to J. M. Briggs on Aug. 21, 1990

This patent is directed to a cable action instrument. The instrument comprises a controller, a reaction end, and an angle adjustment section which connects the controller to the reaction end, and a flexible control cable assembly extending between the controller and the reaction end. The reaction end consists of a scissors tip having a stationary blade and a cable activated blade, both of which have pointed distal ends. A forceps instrument tip having a stationary plant arm and a cable activated arm may be substituted for the scissors tip.

U.S. Pat. No. 4,938,214 issued to P. Specht et al on Jul. 3, 1990

This patent is directed to a hand-held surgical tool. The surgical tool includes an operating end having first and second blade tips which are movable between open and closed positions. When the blade tips are closed, the surgical tool has a needle sharp point having a diameter of only about 50 microns to 2 mm.

U.S. Pat. No. 3,577,991 issued to G. R. Wilkinson on May 11, 1971

This patent is directed to a sewing tissue instrument. The forceps are pivoted together with the outer jaws and a spring set between the members. The thread slides to the end of the forceps and the free end of the thread is pulled through the loops to make a knot.

U.S. Pat. No. 5,196,023 issued to W. Martin on Mar. 23, 1993

This patent is directed to a surgical needle holder and cutter wherein the cutter forming the upper part of the blade has a concave shape. When the forcep jaw is opened, an approximately elliptical opening is formed between the ridge or cutter and the depression into which a thread may be brought from the direction of the opening of the forceps jaw and then can be cut off by closing the jaw.

SUMMARY OF THE INVENTION

The present invention is directed to a suturing method using an improved laparoscopic surgical instrument which permits a surgeon to pass suture without trauma through tissue while retaining the function of grasping the suture. The laparoscopic surgical instrument comprises a modified laparoscopic grasper wherein forcep jaws at the tip are manipulated by means of scissor type handles extending laterally from a tubular housing with an enclosed reciprocating actuating rod connected respectively with the scissor lever arms.

The laparoscopic surgical instrument of the present invention has the tip of the forcep jaws modified to have either a knife, chisel, or cone shaped tip when the jaws are in the closed position. These tips are configured such that they are needle sharp which is critical in reducing trauma and accompanying bleeding and further decreases tissue damage during the suturing procedure.

Another object of the invention is to provide a surgical method for the closure of a surgical incision under direct camera laparoscopic vision of the surgeon, and the closure that is accomplished is a mass closure which allows for closure of peritoneal surfaces as well.

A further object of the invention is to provide a laparoscopic instrument that allows for the rapid control of bleeding from inferior epigastric lacerations or other lacerations of vessels in the outer (or abdominal) wall that may occur with placement of the laparoscopic trocars.

Another object of the invention is to provide a laparoscopic instrument that easily disassembles at the handle and at the interface between the tube member and handle for providing easy access to all the instrument components for cleaning and sterilization prior to surgery.

Still another object of the invention is to provide a laparoscopic instrument having a pair of independently operated actuatable means such that a single instrument can simultaneously perform both the functions of a needle and grasper during laparoscopic surgery.

Yet another object of the present invention is to provide a surgical instrument that works in a similar manner to a needle driver without the requirement for the needle itself in passing suture easily through the fascial and peritoneal surfaces and for retrieving the suture for completing the suture procedure in a rapid, safe and visualized manner.

Accordingly it is an objective of the present invention to provide a method associated with an improved surgical instrument of the standard laparoscopic type grasper that better suits the need of a surgeon for suturing closed, a surgical incision. In addition, it is the objective of the present invention to allow the passage of suture through tissue in order to suture or ligate vessels, approximate tissues and perform all suturing that would require a separate needle driver in laparoscopic surgery. The improvements afforded by this instrument and method will be set forth throughout the following description, claims and accompanying drawings.

BRIEF DESCRIPTION OF THE DRAWINGS

The above, as well as other, advantages of the present invention will become readily apparent to those skilled in the art from the following detailed description of the preferred embodiments when considered in the light of the accompanying drawings in which.

DESCRIPTION OF THE PREFERRED EMBODIMENTS

Figure 1A:
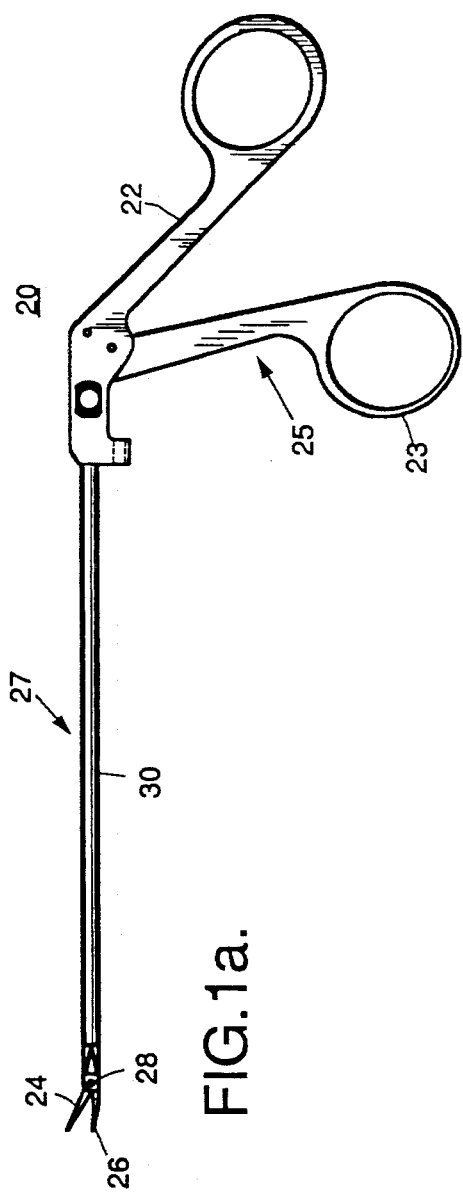
FIG. 1A is a side elevational view of the laparoscopic instrument of the present invention.
Figure 1B:
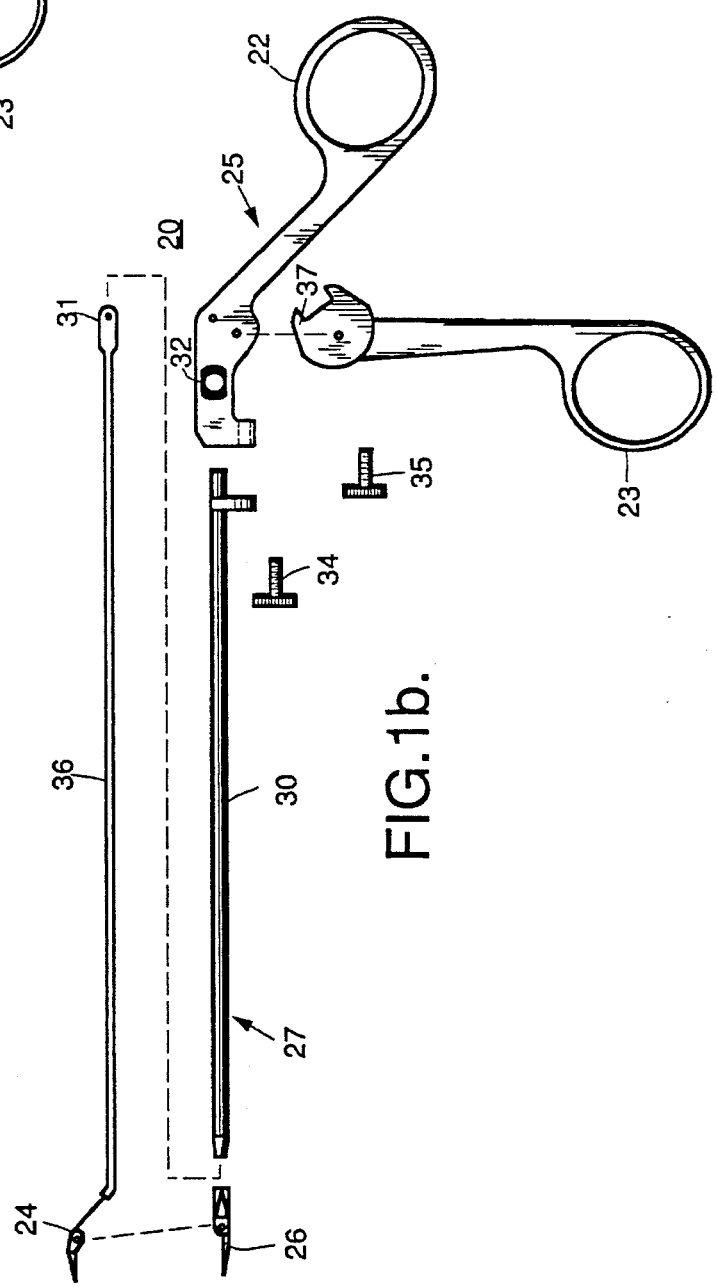
FIG. 1B is an exploded side elevational view of the laparoscopic instrument of FIG. 1A.

Referring now to the drawings wherein like reference numerals refer to like and corresponding parts throughout, the laparoscopic instrument is generally indicated by numeral 20. Referring now to FIGS. 1A and 1B, forcep jaws 24 and 26 are pivoted back and forth in double action movement about an axis defined by pivot pin 28 when actuating rod 36 is reciprocated by a surgeon manipulating the scissor handles 22 and 23 providing a driving means 25 for driving forcep jaws 24 and 26 in a closed position through a patient's skin. Detachable means 27 comprise an elongated tube 30 concentrically sharing an axis with the actuating rod 36 having forcep jaws 24 and 26 engaged at a distal end.

As shown in FIG. 1B, the laparoscopic instrument 20 may be easily disassembled for sterilization prior to surgery in seperating driving means 25 from detachable means 27 by loosening the knurled screw 34 on fixed handle housing 22 and rotating the elongated tube 30 and forcep jaws 24 and 26 slightly, unlatching hook 31 from pin 37 which thereby frees actuating rod 36 and tube 30 from handle housing 22. By loosening thumb screw 35, movable handle or lever means 23 can be disassembled from fixed handle housing 22 that allows for cleaning of the inside of the handle housing area. When dissembled the parts may be flushed, washed and dried according to hospital procedures for stainless steel surgical instruments. A cleaning port 32 may be provided for ease in flushing the disassembled fixed handle housing 22.

Figure 2:
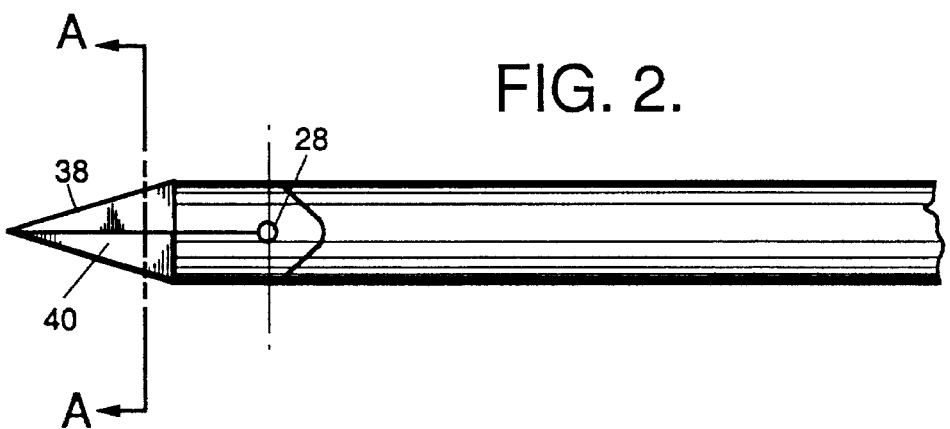
FIG. 2 is a side elevation view, partly in section, of the forcep jaws having a chisel shaped tip.
Figures 3, 6:
FIG. 3 is a cross-sectional view taken along the line A—A in FIG. 2.
FIG. 6 is a cross-sectional view taken along the line B—B in FIG. 5.
Figure 4:
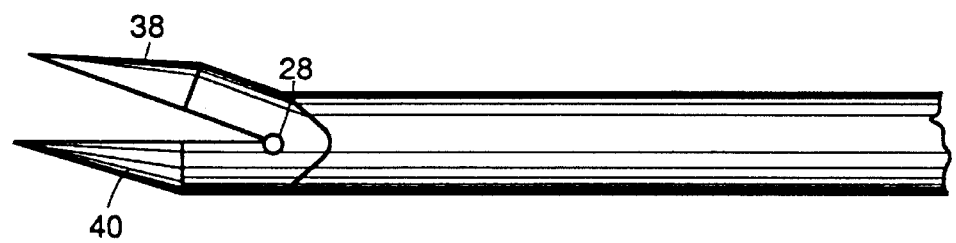
FIG. 4 is a side elevation view, partly in section, of the forcep jaws of FIG. 2 in a completely open condition.

With the above described arrangement, it will be seen that the surgeon is able to selectively operate the scissor handles 22 and 23 to independently open and close the movable forcep jaw 24 in relationship to fixed forcep jaw 26 for grasping, carrying or releasing suture during a laparoscopic operation. To open forcep jaw 24, the surgeon moves movable handle or lever means 23 forward toward the distal end of tube 30. As shown in FIGS. 2 and 3, the forcep jaws 24 and 26 have a chisel shape 38 and 40 which when closed form a chisel shape tip 42. This chisel shape tip 42 operates as a sharp needle point that simultaneously grips and passes the suture through soft tissue. Referring to FIG. 4, chisel shaped jaw 38 pivots open and closed about pivot pin 28 and chisel shaped jaw 40 which is fixed and non-pivotable.

Figure 5:
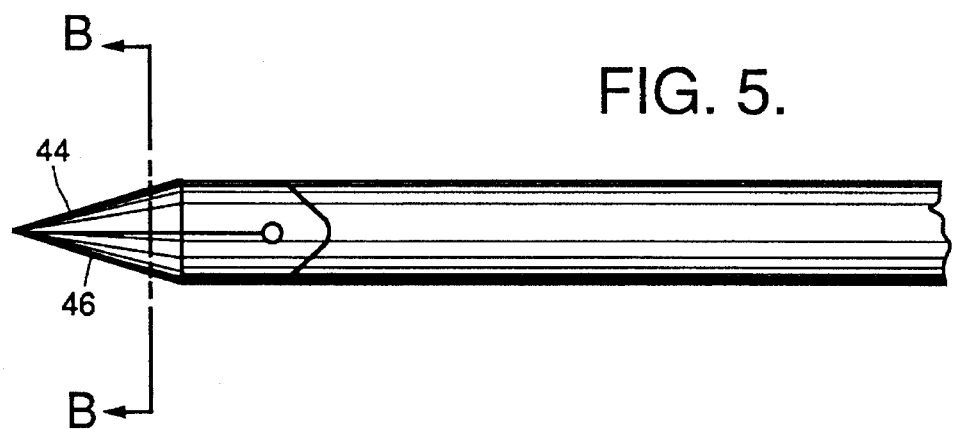
FIG. 5 is a side elevation view, partly in section, of the forcep jaws having a cone shaped tip.
Figure 7:
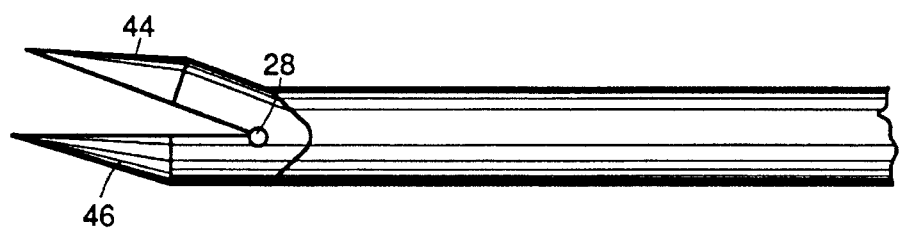
FIG. 7 is a side elevation view, partly in section, of the forcep jaws of FIG. 5 in a completely open condition.
Figure 7A:
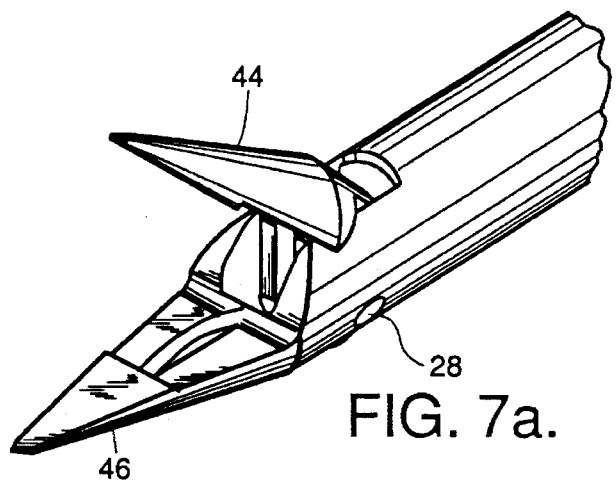
FIG. 7A is a top right perspective view of the forcep of FIG. 7.
Figure 9:
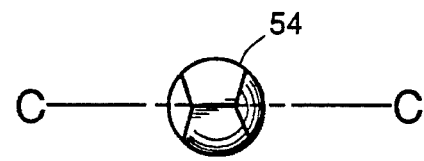
FIG. 9 is a cross-sectional view taken along the line C—C in FIG. 8.
Figure 8:
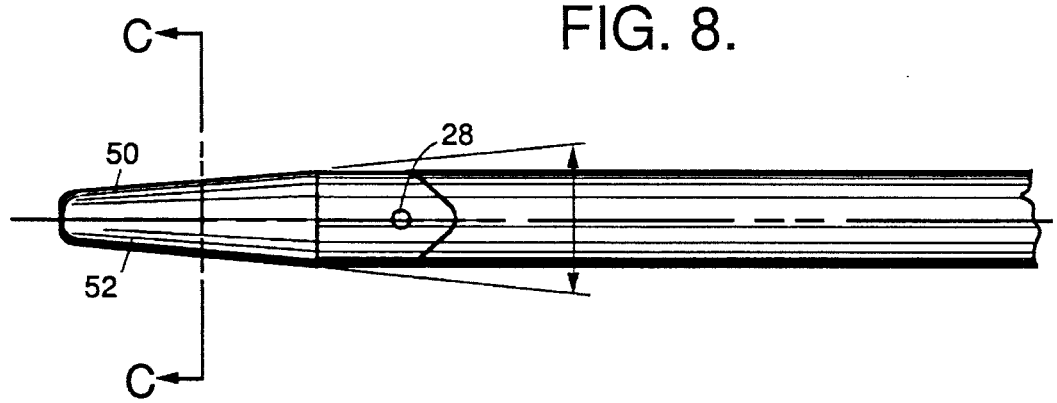
FIG. 8 is a side elevation view, partly in section, of the forcep jaws having a knife shaped tip.
Figure 10:
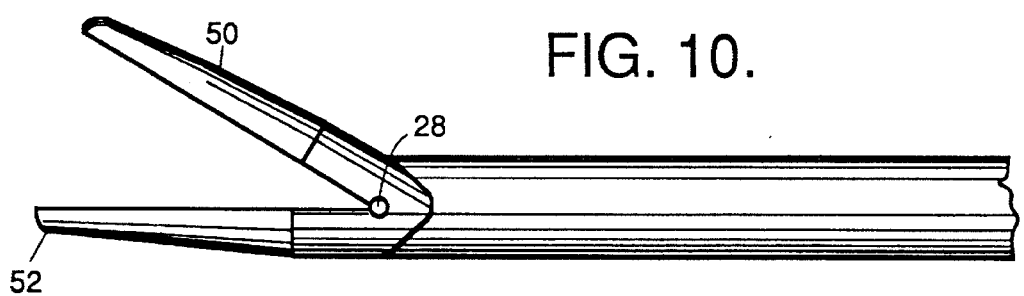
FIG. 10 is a side elevation view, partly in section, of the forcep jaws of FIG. 8 in a completely open condition.

Although the forcep jaws are shown as chisel shaped in FIGS. 2 and 3, they may alternatively have a cone shape 44 and 46 forming a cone shaped tip 48 as shown in FIGS. 5 and 6. Referring to FIG. 7, cone shaped jaw 44 also pivots open and closed about pivot pin 28 and cone shaped jaw 46 which is fixed and non-pivotable. Alternatively, the aforementioned forcep jaws may have a knife shape tip 50 and 52 forming a knife shaped tip 54 as shown in FIGS. 8 and 9. Likewise, as shown in FIG. 10, the knife shaped jaw 50 pivots open and closed about pivot pin 28 and knife shaped jaw 52 which is fixed and non-pivotable. In all the above views, the tips are required to be sharp which is critical in reducing trauma and accompanying bleeding and to decrease tissue damage during the suturing procedure.

Figure 11:
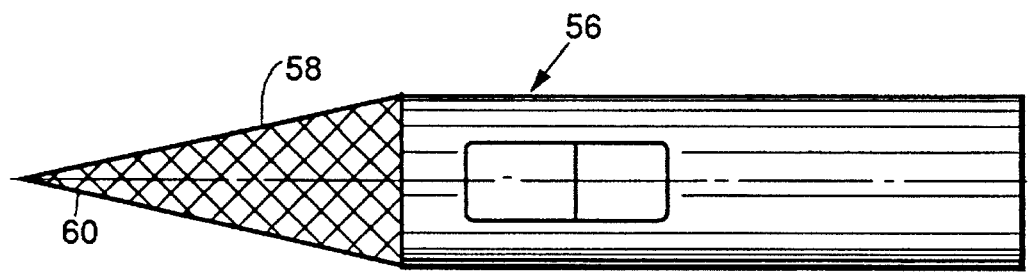
FIG. 11 is a top planar view of the bottom forcep jaw according to one embodiment of the invention.

Common to the various shaped jaw embodiments is a generally partial crosshatched interior jaw surface 58 embedded in jaw body 56 as shown in FIG. 11 which facilitates in grasping more securely the suture material 66 during insertion into tissue. In order to maintain the sharpness of the tip, a partial nonhatched area 60 is provided at the forward end of jaw body 56.

Figure 12:
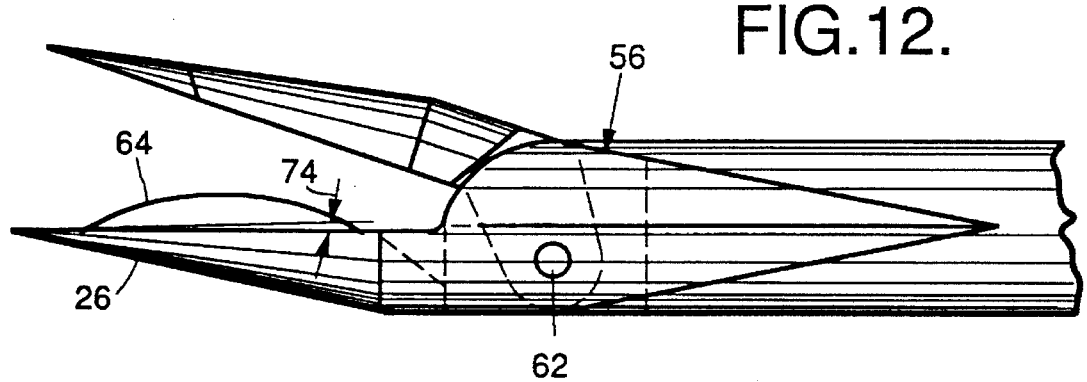
FIG. 12 is a side elevational view, partly in section, of the forcep jaws according to one embodiment of the invention.
Figure 13:
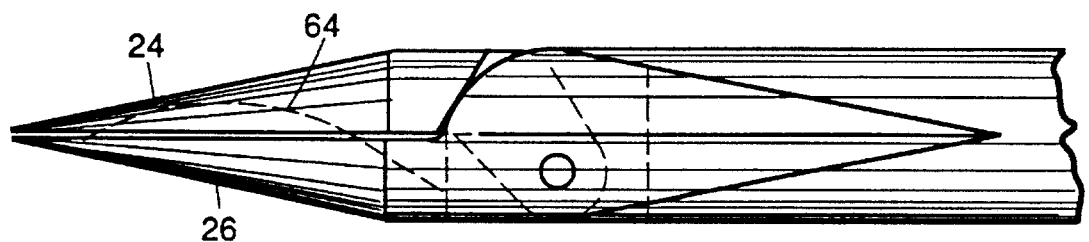
FIG. 13 is a side elevational view, of the forcep jaw of FIG. 12 in a completely closed position.
Figure 13A:
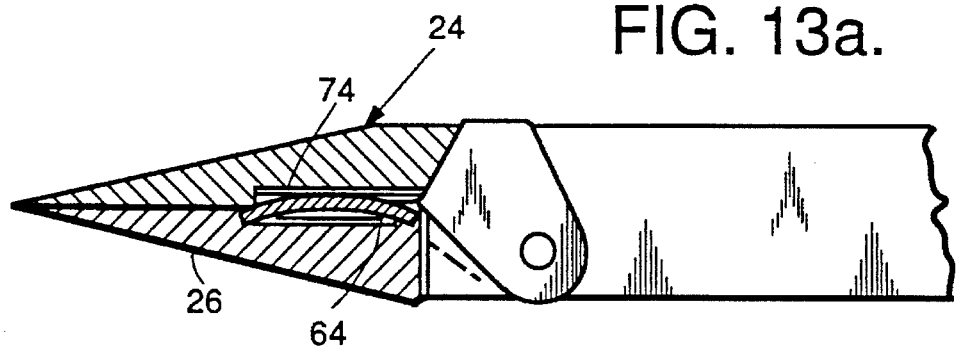
FIG. 13A is a cross-section of the forcep shown in FIG. 13.

FIGS. 12 and 13 show another embodiment of a means to retain the sharpness of the tip at the end of jaw body 56 when the forcep jaws are closed. In FIG. 12 it is seen that lower forcep jaw body 26 is inclined by a small angle, indicated at 74, towards pivot pin hole 62. With this arrangement the small angle 74 accounts for the thickness of the suture such that when the jaws are closed a sharp tip is still defined with the suture grasped resulting from the clearance provided by small angle 74. Additionally, a spring 64 is provided which has one end affixed into jaw body 26 at a point near pivot pin hole 62. The spring 64 assists in more firmly grasping the suture material by adding a compression force resulting in a more positive grip when the jaws 24 and 26 are closed as shown in FIG. 13. The spring 64 is especially useful in handling suture material that is large in diameter, therefore allowing for a wider range of suture sizes that can be used during surgery.

These features and their advantages in use will be more particularly appreciated when reviewing the following method of the present invention used to pass suture through soft tissues during endoscopic/laparoscopic surgery for which the instrument 20 of this invention is provided. In application the surgical instrument 20 is to be grasped by a skilled laparoscopic surgeon and placed for closure of punctured vessels in the muscular surface or for closure of the fascia.

Figure 14A:
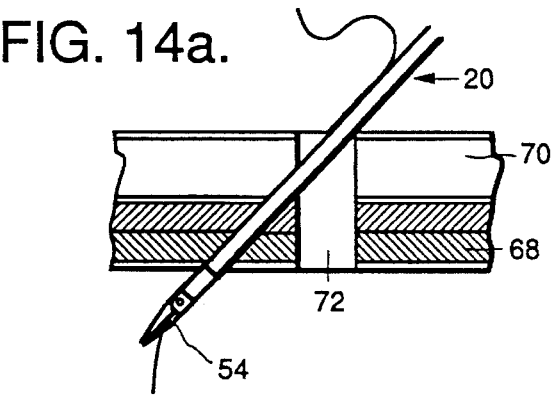
FIG. 14A is a diagrammatic sketch, partly broken away of the tip of the surgical instrument in the closed position passing suture through tissue.
Figure 14B:
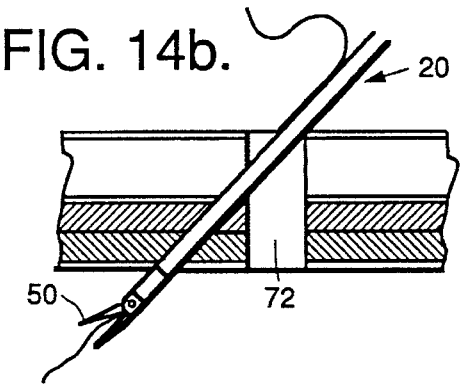
FIG. 14B is a diagrammatic sketch, partly broken away of the tip of the surgical instrument in the open position for dropping the suture.
Figure 14C:
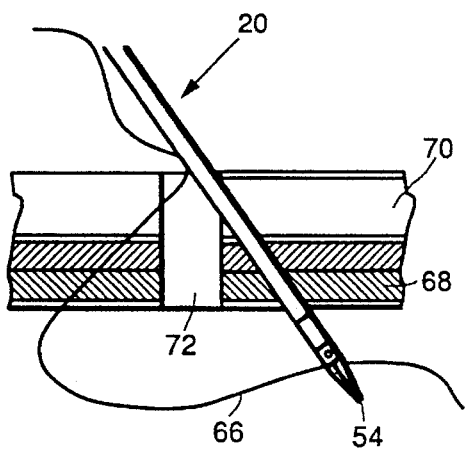
FIG. 14C is a diagrammatic sketch, partly broken away of the tip of the surgical instrument in the closed position passing through tissue at the other side of the incision and picking up suture.
Figure 14D:
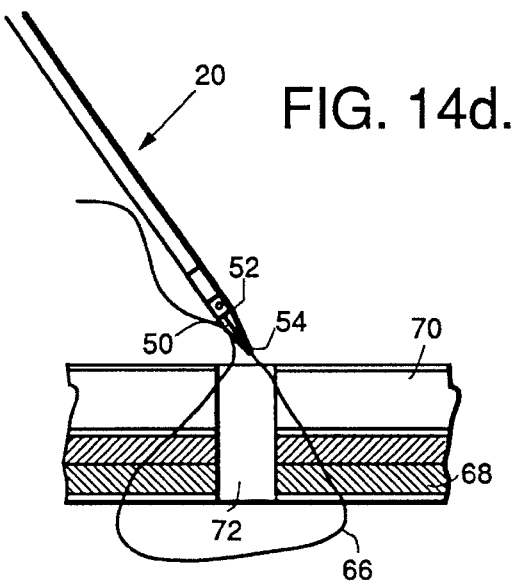
FIG. 14D is a diagrammatic sketch, partly broken away of the tip of the surgical instrument pulling suture through muscle fascia and peritoneum.
Figure 14E:
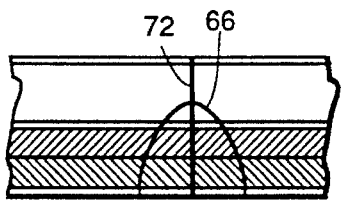
FIG. 14E is a diagrammatic sketch, partly broken away of the suture tied below the skin to complete closure.

FIGS. 14A through 14E are diagrammatic representations of one example of using the method and laparoscopic instrument 20 with the knife shaped tip 54 of the present invention grasping and passing suture through soft tissue for closure of an incision 72. In FIG. 14A the surgeon grasps the suture material 66 with tip 54 and inserts instrument 20 carrying suture material 66 through the muscle fascia 70 and peritoneum 68 until the tip 54 is seen through the peritoneum by direct camera vision. Subsequently, the surgeon releases the suture 66 by opening jaw 50 and withdrawing the instrument 20 out of incision 72 as shown in FIG. 14B. In FIG. 14C the surgeon then takes instrument 20 and inserts the tip 54 through the muscle fascia 70 and peritoneum 68 opposite the first point of insertion grasping the suture 66 with jaws 50 and 52 and pulls the suture 66 carried and held by tip 54 outside incision 72 as shown by FIG. 14D whereupon suture 66 is tied below the skin to complete closure of incision 72 as shown by FIG. 14E.

It is to be pointed out that the knife shaped tip 54 in the above described method may be replaced with either the chisel shape tip 42 or cone shaped tip 48. Although not shown, it may be envisioned in the above described method that a second surgical instrument 20 may be inserted through the muscle fascia 70 and peritoneum 68 opposite the first point of insertion grasping the suture 66 with jaws 50 and 52 and pulling the suture 66 held by tip 54 outside incision 72 by either an assistant or the surgeon resulting in a savings of time for completion of the closure.

By way of example but not of limitation, it has been shown that by using the present invention during a laparoscopic assisted vaginal hysterectomy, the total time required for the closure of the two 12 mm and one 10 mm trocar ports has been reduced from 15 minutes (as required by prior surgical procedures) to 3 minutes.

There has been described and illustrated herein an improved laparoscopic instrument and surgical method. While particular embodiments of the invention have been described, it is not intended that the invention be limited exactly thereto, as it is intended that the invention be as broad in scope as the art will permit. The foregoing description and drawings will suggest other embodiments and variations within the scope of the claims to those skilled in the art, all of which are intended to be included in the spirit of the invention as herein set forth.

What is claimed is:

1. A laparoscopic instrument for grasping, carrying and passing suture through a patient's skin for suturing an open wound comprising:

a hollow tube having a first end and a second end;

a first jaw element having a tip end and a base section, said base section fixedly engaging said first end of said hollow tube and including a pivot rod means, said tip end tapering downwardly to said base section and defining a lower surface, said lower surface partially cross hatched having a partial nonhatched area at said tip end, said lower surface having an arcuate spring attached thereto from said tip end to said base section;

a second jaw element having a pivot hole pivotally engaging said pivot rod means of said base section of said first jaw element, and a second through-hole in said second jaw element;

a thin wire rod having a first and second end, said first end of said rod having engaging means, said engaging means engaging said second through-hole in said second jaw element; and driving means engaging said second end of said rod for imparting reciprocal motion to said rod relative to said tube for pivotal motion of said second jaw element, wherein said second jaw element pivotally engages said first jaw element defining a shaped tip for grasping, carrying and passing the suture through a patient's skin for suturing an open wound and said tube, rod, first and second jaw elements and said actuating means detachable for cleaning.

2. A laparoscopic instrument for passing through a patient's peritoneum and fascia, and closing an open wound with suture material comprising:

(a) detachable piercing, carrying and grasping means having a sharp tip for insertion below skin level and grasping and carrying the suture material;

(b) driving means for driving said detachable means through the patient's peritoneum and fascia at a first point and actuating said detachable means for gripping the suture material, said detachable piercing and grasping means comprises first and second forcep jaws pivotally engaged to each other, said first jaw fixedly engaging a hollow tube and said second jaw engaging a thin wire rod concentrically located within said hollow tube;

(c) said first and second forcep jaws comprising interior upper and lower jaw surfaces having partially knurled areas and a partially unknurled area at a tip point, said upper and lower interior jaw surfaces are inclined downwardly by a small angle from said tip point to the rear of said jaw surfaces; and (d) said lower interior jaw surface bas an arcuate spring attached thereto from said tip point to the rear of said jaw surfaces for gripping various size suture while allowing the jaws to close completely, whereby the suture material is carried by said detachable means and recovered by driving said detachable means through the patient's peritoneum and fascia at a second point and actuating said detachable means for gripping and pulling the suture material outside the wound providing for rapid closure of the open wound.

3. A laparoscopic instrument according to claim 2, wherein said detachable piercing and grasping means comprises a laparoscopic grasper defining a sharp knife shaped tip at a distal end.

4. A laparoscopic instrument according to claim 2, wherein said detachable piercing and grasping means comprises a laparoscopic grasper defining a sharp cone shaped tip at a distal end.

5. A laparoscopic instrument according to claim 2, wherein said detachable piercing and grasping means comprises a laparoscopic grasper defining a sharp chisel shaped tip at a distal end.

6. A laparoscopic instrument according to claim 2, wherein said driving means comprises a housing means and a lever means pivotally engaging said housing means, wherein said lever means detachable from said housing means for cleaning prior to surgery.

7. A laparoscopic instrument for grasping, carrying and passing suture through a patient's skin for suturing an open wound comprising:

a hollow tube having a first end and a second end;

a first jaw element having a tip end and a base section, said base section fixedly engaging said first end of said hollow tube and including a pivot rod means, said tip end tapering downwardly to said base section;

a second jaw element having a pivot hole pivotally engaging said pivot rod means of said base section of said first jaw element;

a thin wire rod having a first and second end, said first end of said rod having engaging means for engaging said second jaw element;

driving means engaging said second end of said rod for imparting reciprocal motion to said rod relative to said tube for pivotal motion of said second jaw element, said driving means comprises a housing means fixedly engaging said second end of said hollow tube and a lever means fixedly engaging said second end of said rod and pivotally engaging said housing means, said housing means detachable from said second end of said hollow tube and said lever means detachable from said second end of said rod and housing means; and said base section of said first jaw element detachable from said first end of said hollow tube and said second jaw element detachable from said pivot rod means of said base section and said engaging means of said first end of said rod, whereby said second jaw element pivotally engages said first jaw element defining a shaped tip for grasping, carrying and passing the suture through a patient's skin for suturing an open wound and said tube, rod, first and second jaw elements and said engaging means detachable for cleaning.

8. An instrument for grasping, carrying, and passing suture through a patient's tissue comprising (a) a handle/actuator means for holding and activating the instrument from a closed to an open position and vice-versa; and (b) a forcep means which opens and closes for grasping the suture and having forcep jaws with a tapering end for insertion into a place of suturing, and wherein said forcep means holds the suture in a fully closed position while carrying the suture without displacement of the forcep jaws, and allowing said tapering end to be insertable through the patient's tissue to the place of suturing.

* * * * *